United States Patent [19]
Fujikawa et al.

[11] Patent Number: 5,935,608
[45] Date of Patent: Aug. 10, 1999

[54] ANTIBACTERIAL TITANIA AND PROCESS FOR PRODUCING THE SAME

[75] Inventors: Hideki Fujikawa; Katsuyuki Tanabe, both of Tokyo, Japan

[73] Assignee: Nittetsu Mining Co., Ltd., Tokyo, Japan

[21] Appl. No.: 08/842,532

[22] Filed: Apr. 15, 1997

[30] Foreign Application Priority Data

Apr. 15, 1996 [JP] Japan ................................. 8-092485

[51] Int. Cl.$^6$ .......................... A01N 59/16; A01N 25/08; A01N 25/26; C01G 23/047
[52] U.S. Cl. .......................... 424/618; 424/600; 424/617; 424/641; 424/642; 424/643; 424/678; 424/681; 424/685; 424/666; 424/401; 424/404; 424/409; 424/421
[58] Field of Search .................... 424/409, 600, 424/617, 618, 641, 642, 643, 678, 681, 685, 666, 401, 404, 421

[56] References Cited

U.S. PATENT DOCUMENTS

| | | | |
|---|---|---|---|
| 4,798,813 | 1/1989 | Kato et al. | 502/60 |
| 5,413,788 | 5/1995 | Edwards et al. | 424/409 |
| 5,503,840 | 4/1996 | Jacobson et al. | 424/421 |

FOREIGN PATENT DOCUMENTS

| | | |
|---|---|---|
| 0734651 | 10/1996 | European Pat. Off. . |
| 0251783 | 1/1998 | European Pat. Off. . |
| 06298532 | 10/1994 | Japan . |
| WO9324103 | 12/1993 | WIPO . |
| WO9702038 | 1/1997 | WIPO . |

OTHER PUBLICATIONS

Corbett, Richard J. "A novel inorganic preservative system for personal care products," Cosmetic News, vol. 19 (106), 1996, pp. 20–25.

Corbett, R.J. "An Inorganic biocide using a novel presentation of silver," International Journal of Cosmetic Science, vol. 18(4), 1996, pp. 151–165.

*Primary Examiner*—John Pak
*Attorney, Agent, or Firm*—Sughrue, Mion, Zinn, Macpeak & Seas, PLLC

[57] ABSTRACT

An antibacterial titania comprising a titania to which ions of an antibacterial metal are adhered, wherein the antibacterial metal is silver; and the antibacterial titania further contains chlorine at a Cl/Ag molar ratio in a range of from 2.8 to 7.2. A process for producing an antibacterial titania which comprises the steps of: (1) incorporating a salt of an antibacterial metal into a slurry of metatitanic acid to adhere ions of the antibacterial metal to titania in the metatitanic acid slurry; and (2) adding a source of chlorine ions to the slurry, wherein the antibacterial metal is silver.

5 Claims, No Drawings

US 5,935,608

ANTIBACTERIAL TITANIA AND PROCESS FOR PRODUCING THE SAME

FIELD OF THE INVENTION

The present invention relates to an antibacterial titania which does not discolor upon exposure to various ultraviolet rays, e.g., sunlight, or heat and has excellent antibacterial properties. The-present invention also relates to a process for producing the same.

BACKGROUND OF THE INVENTION

It has conventionally been known that silver, copper, zinc, and ions of these metals have an antibacterial activity. Typical application examples for metallic antibacterial agents utilizing the antibacterial activity of ions of these metals include a catheter having silver particles adhered to the surface thereof (see U.S. Pat. No. 4,054,139) and a method of coating a medical polymer material with a salt of a metal such as silver, zinc, or cerium (see U.S. Pat. No. 4,612,337 and JP-A-62-11457 (the term "JP-A" as used herein means an "unexamined published Japanese patent application")). However, these prior art techniques have not been put to practical use, most likely due to poor particle properties, e.g., insufficient fineness or insufficient dispersibility, of the metal or other powder used.

Various antibacterial agents have been proposed which comprise inorganic compounds having ions of silver, copper or zinc adhered thereto or held thereon through ion exchange. Attempts are being made to incorporate ions of a metal such as silver into natural and synthetic zeolites through ion exchange and to use these zeolites as antibacterial agents in applications such as industrial articles, daily necessaries, or medical articles (see, for example, JP-B-63-54013 (the term "JP-B" as used herein means an "examined Japanese patent publication")).

In particular, an example of the synthesis of an antibacterial titania has been disclosed which comprises adding ammonia water to an aqueous solution of titanium trichloride in the presence of an alcohol to synthesize a white porous titania gel, and then causing this gel to adsorb antibacterial metal ions such as silver ions or/and zinc ions (see JP-A-5-4816). This antibacterial titania having antibacterial metal ions adsorbed thereto has an advantage in that since the antibacterial titania itself is dispersible into a colloidal state, an antibacterial composition containing the titania evenly and stably dispersed therein can be obtained.

Examples of use of antibacterial agents have been disclosed which include: a technique of dispersing such an antibacterial composition into a molten resin to form a resin molding having antibacterial properties; a technique of preparing a paint containing an antibacterial agent stably dispersed therein and applying the paint to a building to impart antibacterial properties thereto; a technique of adhering an antibacterial titania to fibers and using the fibers as a building material such as a wall paper; and a technique of incorporating an antibacterial titania into a resin and forming the resin into an antibacterial wrapping material for foods (see JP-A-4-231063). Further, an antibacterial titania (anatase titania having an antibacterial metal adhered thereto) having satisfactory antibacterial-metal dispersibility and sufficient particle fineness of the antibacterial agent itself and capable of being stably produced at low cost was disclosed recently (see JP-A-6-298532).

However, the antibacterial titania having adhered thereto silver ions, which are thought to have a relatively high antibacterial activity among ions of the metals enumerated above, has a drawback that since silver ions are unstable to ultraviolet rays and heat and are hence apt to be reduced into silver upon ultraviolet irradiation or heating, the color of the antibacterial titania containing silver ions changes into light black or gray. Consequently, the products containing an antibacterial agent comprising silver ions suffer discoloration upon exposure to light or heat resulting in an impaired commercial value, and hence they should be used in limited situations. Another drawback thereof is that the reduction of the silver ions adhered to titania into silver metal results in reduced antibacterial properties.

SUMMARY OF THE INVENTION

An object of the present invention is to provide an antibacterial titania which neither discolors upon irradiation with various ultraviolet rays, e.g., sunlight, or heating, nor suffers the deterioration in antibacterial properties caused by reduction of silver ions into silver metal.

Another object of the present invention is to provide a process for producing the antibacterial titania.

These and other objects of the present invention have been attained by an antibacterial titania comprising a titania to which ions of an antibacterial metal are adhered, wherein the antibacterial metal is silver; and the antibacterial titania further contains chlorine at a Cl/Ag molar ratio in a range of from 2.8 to 7.2.

Furthermore, these and other objects of the present invention have been attained by a process for producing an antibacterial titania which comprises the steps of:

(1) incorporating a salt of an antibacterial metal into a slurry of metatitanic acid to adhere ions of the antibacterial metal to titania in the metatitanic acid slurry; and (2) adding a source of chlorine ions to the slurry, wherein the antibacterial metal is silver.

DETAILED DESCRIPTION OF THE INVENTION

An advantage of the process of the present invention resides in that both silver ions and chlorine ions are added to a slurry of metatitanic acid, a titanium compound. In the present invention, the pH of the slurry is preferably regulated to a weakly alkaline range of from 7 to 9 with a caustic alkali solution. Furthermore, silver ions and chlorine ions are preferably mixed so that the Cl/Ag molar ratio is in a range of from 2.8 to 7.2.

Maintaining the slurry medium weakly alkaline with an aqueous alkali solution is thought to function as follows. In the case of a slurry medium having a pH value on the acid side, the titania surface usually has a positive zeta-potential, so that silver ions, which have positive electrical charges, are less adsorbed onto the surface or inner parts of the titania. In contrast, when the pH of the slurry medium shifts to a value close to the alkaline side, the zeta-potential of the titania surface shifts from a positive to a negative value. The zeta-potential of the titania surface reaches its maximum around a weakly alkaline region. This means that the amount of silver ions adsorbed onto the titania surface will approach a maximum around that pH region. Therefore, the regulation of the pH of the solution to a value in a weakly alkaline region is intended to increase the adsorption amount of silver.

However, if the pH of the slurry medium further shifts to the strongly alkaline side, silver ions react with the excess hydroxide ions present in the solution to yield silver hydroxide, or silver oxide, and this ultimately discolors the solution. The aqueous alkali solution for use in the present invention is desirably an aqueous solution of either an alkali metal hydroxide or an alkaline earth metal hydroxide. Especially suitable of these hydroxides are caustic soda and caustic potash, which have high solubility. With respect to the chlorine ions to be added, there are no particular limitations on chlorine sources, and use may be made of zinc chloride, calcium chloride, magnesium chloride, aluminum chloride, hydrochloric acid, or the like. However, zinc chloride is preferred because it provides the best antibacterial properties. It should be noted that if zinc nitrate or zinc oxide is used -in place of zinc chloride, the titania yielded is gray and is not a desirable product. Thus, neither nitrate ions nor oxygen ions can be the ions used in combination with an antibacterial metal.

The concentration of the metatitanic acid in the slurry is not particularly limited; however, it is preferably from 1 to 80 wt. %, and more preferably from 5 to 50 wt. %. The salt of an antibacterial metal is not particularly limited; however, the silver salt is preferably a water-soluble silver salt, and examples thereof include silver nitrate, silver sulfate, silver acetate, silver diamine nitrate, and silver diamine sulfate. When the salt of an antibacterial metal is added to the slurry, the concentration in terms of silver is preferably from 0.01 to 50 wt. %, more preferably from 0.1 to 30 wt. %, per the solid content of the metatitanic acid.

In the present invention, the grain size of the starting material, the final product and the like is not particularly limited; however, those having a smaller grain size are preferably used. That is, the smaller the grain size is, the larger the specific surface area is, and therefore, the larger the amount of the silver adhered is. Generally, the final product of the present invention has a grain size of several micrometers or less.

The antibacterial titania of the present invention is characterized in that it exhibits excellent antibacterial activity when incorporated in various resins, fibers, paints, sealing materials, etc., and in that it suffers no discoloration because of its excellent light and heat resistance.

The antibacterial titania produced according to the process of the present invention, in which silver ions, a solution of a caustic alkali, and chlorine ions are incorporated into a slurry of metatitanic acid and the final pH of the slurry medium is adjusted to from 7 to 9, is at least equal in antibacterial properties to conventional antibacterial titanias obtained by adhering antibacterial metal ions to titania.

The conventional antibacterial titanias are apt to discolor with the passage of time by the action of ultraviolet rays, e.g., sunlight, and heat, whereas the antibacterial titania obtained through the procedure according to the present invention is significantly inhibited from discoloring.

Examples of processes for producing powders of the antibacterial titania of the present invention and comparative titania powders are shown below. However, the present invention should not be construed as being limited to the following samples.

EXAMPLES

In the following samples, powders of antibacterial titania, titania, etc. were evaluated for antibacterial properties by a method which is the same as the method for determining "minimum inhibitory concentration (MIC)" for *Escherichia coli* as established by the Chemotherapy Society of Japan and described in JP-A-5-4816, except that the method was modified so as to be applicable to water-insoluble agents such as the antibacterial titania of the present invention.

Namely, the evaluation method comprises placing a test sample (e.g., an antibacterial titania) in an Erlenmeyer flask, sterilizing the sample and the flask with high-pressure steam, subsequently introducing MH culture medium into the flask, adding an inoculation bacterium liquid having a cell concentration of 106 per ml, shaking the flask at 37° C. for 20 hours, and then examining the bacterium liquid with a microscope to judge as to whether the number of cells has increased or not, to thereby determine the minimum inhibitory concentration (MIC) which resulted in negative bacterial growth. The light resistance of the samples was evaluated by measuring the whiteness (WH) thereof before and after irradiation with sunlight (ultraviolet rays) (standing for 2 days at a window on which sunlight struck) and comparing the observed values. The heat resistance of the samples was likewise evaluated by measuring the whiteness (WH) thereof before and after heating (230° C., 3 hours) and comparing the observed values. The acceptable whiteness values for the. samples prior to irradiation with sunlight and heating are 95 and higher.

The whiteness of the samples is expressed in terms of brightness by Hunter, which is calculated from values of a three-dimensional color coordinate system (L, a, b) obtained with a color-difference meter (e.g., fully automatic color-difference meter "Color Ace" Type TC-8600, manufactured by Tokyo Denshoku Co., Ltd.).

The slurry of metatitanic acid for use in the present invention is obtained by adding an alkali hydroxide or ammonia to an aqueous solution of a water-soluble titanium salt, e.g., $TiCl_4$, $Ti(NO_3)_4$, or $Ti(SO_4)_2$. The slurried titania, which is an intermediate for $TiO_2$, consists of fine particles of hydrous anatase titanium dioxide ($TiO_2 \cdot xH_2O$), which dissolve in both acids and concentrated alkali solutions.

SAMPLE 1

To 60 g of a 30 wt. % metatitanic acid slurry at room temperature were added, with stirring, 111 ml of a 0.066 mol/l aqueous silver nitrate solution and 372 ml of a 0.050 mol/l aqueous zinc chloride solution. The final pH of the slurry was adjusted to a weakly alkaline value (pH=8.4) with an aqueous caustic soda solution. This slurry was stirred at room temperature for 3 hours. After the stirring was stopped, the slurry was allowed to stand for 1 hour and then filtered with suction. The resulting residue was washed with water and dried at 110° C. for 24 hours to obtain a powder (hereinafter referred to as "powder 1"). The contents of the adhered silver and chlorine in powder 1 were 4.6% by weight and 7.5% by weight, respectively, and the whiteness (WH) of powder 1 was 96.

SAMPLE 2

To 60 g of a 30 wt. % metatitanic acid slurry at room temperature was gradually added, with stirring, 111 ml of a 0.066 mol/l aqueous silver nitrate solution. Subsequently, 396 ml of a 0.050 mol/l aqueous zinc chloride solution was gradually added thereto while keeping the pH of the slurry medium at a weakly alkaline value (pH=7.9) with an aqueous ammonia solution. This slurry was stirred at room temperature for 3 hours. After the stirring was stopped, the slurry was allowed to stand for 1 hour and then filtered with suction. The resulting residue was washed with water and dried at 110° C. for 24 hours to obtain a powder (hereinafter referred to as "powder 2"). The contents of the adhered silver and chlorine in powder 2 were 3.6% by weight and 8.4% by weight, respectively, and the whiteness (WH) of powder 2 was 92.

SAMPLE 3

An aqueous ammonia solution was gradually added to 60 g of a 30 wt. % metatitanic acid slurry at room temperature with stirring to thereby adjust the pH of the slurry to a weakly alkaline value (pH=8.2). After completion of the pH adjustment, the slurry obtained was filtered with suction. The resulting residue was washed with water and dried at 110° C. for 24 hours to obtain a powder (hereinafter referred to as "powder 3").

SAMPLE 4

An aqueous caustic soda solution was gradually added to 60 g of a 30 wt. % metatitanic acid slurry at room temperature with stirring to thereby adjust the pH of the slurry to a weakly alkaline value (pH=7.9). After completion of the pH adjustment, the slurry obtained was filtered with suction. The resulting residue was washed with water and dried at 110° C. for 24 hours to obtain a powder (hereinafter referred to as "powder 4").

SAMPLE 5

To 60 g of a 30 wt. % metatitanic acid slurry at room temperature was gradually added, with stirring, 111 ml of a 0.066 mol/l aqueous silver nitrate solution. The pH of this slurry was adjusted to a weakly alkaline value (pH=8.6) with an aqueous ammonia solution. The pH-adjusted slurry was stirred at room temperature for 3 hours. After the stirring was stopped, the slurry was allowed to stand for 1 hour and then filtered with suction. The resulting residue was washed with water and dried at 110° C. for 24 hours to obtain a powder (hereinafter referred to as "powder 5"). The content of the adhered silver in powder 5 was 3.8% by weight, and the whiteness (WH) of powder 5 was 87.

SAMPLE 6

To 60 g of a 30 wt. % metatitanic acid slurry at room temperature was gradually added, with stirring, 111 ml of a 0.066 mol/l aqueous silver nitrate solution. The pH of this slurry was adjusted to a weakly alkaline value (pH=7.8) with an aqueous caustic soda solution. The pH-adjusted slurry was stirred at room temperature for 3 hours. After the stirring was stopped, the slurry was allowed to stand for 1 hour and then filtered with suction. The resulting residue was washed with water and dried at 110° C. for 24 hours to obtain a powder (hereinafter referred to as "powder 6"). The content of the adhered silver in powder 6 was 4.0% by weight, and the whiteness (WH) of powder 6 was 87.

SAMPLES 7 TO 10

To 60 g of a 30 wt. % metatitanic acid slurry at room temperature was gradually added, with stirring, 111 ml of a 0.066 mol/l aqueous silver nitrate solution. Subsequently, a 0.050 mol/l aqueous zinc chloride solution was gradually added thereto in amounts of 210 ml (Sample 7), 540 ml (Sample 8), 810 ml (Sample 9), and 70 ml (Sample 10), respectively, while keeping the pH of the slurry at a weakly alkaline value (pH=7.5) with an aqueous caustic soda solution. Each slurry was stirred at room temperature for 3 hours. After the stirring was stopped, the slurries were allowed to stand for 1 hour and then filtered with suction. The resulting residues were washed with water and dried at 110° C. for 24 hours. Thus, powders (hereinafter referred to as "powder 7" to "powder 10") were obtained.

SAMPLE 11

To 60 g of a 7.5 wt. % metatitanic acid slurry at room temperature was gradually added, with stirring, 28 ml of a 0.066 mol/l aqueous silver nitrate solution. Subsequently, 116 ml of a 0.050 mol/l aqueous zinc chloride solution was gradually added thereto while keeping the pH of the slurry at a weakly alkaline value (pH=8.5) with an aqueous caustic soda solution. This slurry was stirred at room temperature for 3 hours. After the stirring was stopped, the slurry was allowed to stand for 1 hour and then filtered with suction. The resulting residue was washed with water and dried at 110° C. for 24 hours to obtain a powder (hereinafter referred to as "powder 11"). The contents of the adhered silver and chlorine in powder 11 were 3.2% by weight and 6.7% by weight, respectively, and the color tone of powder 11 prior to irradiation with sunlight was white.

SAMPLES 12 TO 16

To 60 g of a 7.5 wt. % metatitanic acid slurry at room temperature was gradually added, with stirring, 28 ml of a 0.066 mol/l aqueous silver nitrate solution. Subsequently, a 0.050 mol/l aqueous zinc nitrate solution was gradually added thereto in amounts of 18 ml (Sample 12), 55 ml (Sample 13), 95 ml (Sample 14), 137 ml (Sample 15), and 207 ml (Sample 16), respectively, while keeping the pH of the slurry at a weakly alkaline value (pH=7.8) with an aqueous caustic soda solution. Each slurry was stirred at room-temperature for 3 hours. After the stirring was stopped, the slurries were allowed to stand for 1 hour and then filtered with suction. The resulting residues were washed with water and dried at 110° C. for 24 hours. Thus, powders (hereinafter referred to as "powder 12" to "powder 16") were obtained.

SAMPLE 17

To 56 g of a 30 wt. % metatitanic acid slurry at room temperature was gradually added, with stirring, 201 ml of a 0.066 mol/l aqueous silver nitrate solution. Subsequently, 2.96 g of a zinc oxide powder was gradually added thereto while keeping the pH of the slurry at a weakly alkaline value (pH=8.3) with an aqueous caustic soda solution. This slurry was stirred at room temperature for 3 hours. After the stirring was stopped, the slurry was allowed to stand for 1 hour and then filtered with suction. The resulting residue was washed with water and dried at 110° C. for 24 hours to obtain a powder (hereinafter referred to as "powder 17"). The color tone of powder 17 prior to irradiation with sunlight was gray.

SAMPLE 18

To 28 g of a 30 wt. % metatitanic acid slurry at room temperature was gradually added, with stirring, 100 ml of a 0.066 mol/l aqueous silver nitrate solution. Subsequently, 356 ml of a 0.05 mol/l aqueous calcium chloride solution was gradually added thereto while keeping the pH of the slurry at a weakly alkaline value (pH=8.2) with an aqueous caustic soda solution. This slurry was stirred at room temperature for 3 hours. After the stirring was stopped, the slurry was allowed to stand for 1 hour and then filtered with suction. The resulting residue was washed with water and dried at 110° C. for 24 hours to obtain a powder (hereinafter referred to as "powder 18"). The contents of the adhered silver and chlorine in this powder were 2.9% by weight and 5.2% by weight, respectively, and the color tone of powder 18 prior to irradiation with sunlight was white.

SAMPLE 19

To 28 g of a 30 wt. % metatitanic acid slurry at room temperature was gradually added, with stirring, 100 ml of a 0.066 mol/l aqueous silver nitrate solution. Subsequently, 392 ml of a 0.05 mol/l aqueous magnesium chloride solution was gradually added thereto while keeping the pH of the slurry at a weakly alkaline value (pH=7.9) with an aqueous caustic soda solution. This slurry was stirred at room temperature for 3 hours. After the stirring was stopped, the slurry was allowed to stand for 1 hour and then filtered with suction. The resulting residue was washed with water and dried at 110° C. for 24 hours to obtain a powder (hereinafter referred to as "powder 19"). The contents of the adhered silver and chlorine in this powder were 3.0% by weight and 5.6% by weight, respectively, and the color tone of powder 19 prior to irradiation with sunlight was white.

SAMPLE 20

To 28 g of a 30 wt. % metatitanic acid slurry at room temperature was gradually added, with stirring, 100 ml of a 0.066 mol/l aqueous silver nitrate solution. Subsequently, 353 ml of a 0.05 mol/l aqueous aluminum chloride solution was gradually added thereto while keeping the pH of the slurry at a weakly alkaline value (pH=8.1) with an aqueous caustic soda solution. This slurry was stirred at room temperature for 3 hours. After the stirring was stopped, the slurry was allowed to stand for 1 hour and then filtered with suction. The resulting residue was washed with water and dried at 110° C. for 24 hours to obtain a powder (hereinafter referred to as "powder 20"). The contents of the adhered silver and chlorine in this powder were 2.8% by weight and 5.1% by weight, respectively, and the color tone of powder 20 prior to irradiation with sunlight was white.

SAMPLE 21

To 50 g of a 30 wt. % metatitanic acid slurry at room temperature was gradually added, with stirring, 50 ml of a 0.066 mol/l aqueous silver nitrate solution. Subsequently, 20 ml of a 1.0 mol/l aqueous hydrochloric acid solution was gradually added thereto while keeping the pH of the slurry at a weakly alkaline value (pH=8.6) with an aqueous caustic soda solution. This slurry was stirred at room temperature for 3 hours. After the stirring was stopped, the slurry was allowed to stand for 1 hour and then filtered with suction. The resulting residue was washed with water and dried at 110° C. for 24 hours to obtain a powder (hereinafter referred to as "powder 21"). The contents of the adhered silver and chlorine in this powder were 3.1% by weight and 5.6% by weight, respectively, and the color tone of powder 21 prior to irradiation with sunlight was white.

Table 1 provides a comparison among samples 1 to 6 (powders 1 to 6) with respect to the effects of the type of pH regulator solution used and the use of chlorine in the preparation of these powders on light resistance, heat resistance, and minimum inhibitory concentration (MIC) for *Escherichia coli*.

TABLE 1

| Sample No. | Powder No. | pH Regulator Solution (alkali solution) | Component (wt %) Ag | Component (wt %) Cl | Cl/Ag Molar Ratio | Light Resistance (WH) before sunlight irradiation | Light Resistance (WH) after sunlight irradiation | Heat Resistance (WH) before heating | Heat Resistance (WH) after heating | Antibacterial Property MIC (ppm) | Evaluation |
|---|---|---|---|---|---|---|---|---|---|---|---|
| 1 (Inv)  | 1 | NaOH | 4.6 | 7.5 | 5.14 | 96 | 95 | 96 | 95 | 250 | good |
| 2 (Comp) | 2 | NH$_3$ | 3.6 | 8.4 | 7.50 | 92 | 89 | 92 | 89 | 250 | bad |
| 3 (Comp) | 3 | NH$_3$ | — | — | — | 96 | 96 | 96 | 96 | ineffective | bad |
| 4 (Comp) | 4 | NaOH | — | — | — | 97 | 96 | 97 | 94 | ineffective | bad |
| 5 (Comp) | 5 | NH$_3$ | 3.8 | — | — | 87 | 87 | 87 | 87 | 250 | bad |
| 6 (Comp) | 6 | NaOH | 4.0 | — | — | 87 | 85 | 87 | 87 | 250 | bad |

(Note)
Inv: Invention, Comp: Comparison

Table 1 shows the following. Sample 1 was excellent in antibacterial properties, light resistance, and heat resistance, whereas sample 2 had a slightly poor powder whiteness and insufficient light and heat resistance because of the use of ammonia for pH adjustment, although it was sufficiently effective in antibacterial properties. Further, samples 3 and 4 were ineffective in antibacterial properties, while samples 5 and 6 had poor light and heat resistance although they were effective in antibacterial properties.

Table 2 provides a comparison among samples 7 to 10 (powders 7 to 10) and samples 4 and 6 (powders 4 and 6) with respect to the effects of the contents of silver and chlorine in these powders on light resistance, heat resistant, and minimum inhibitory concentration (MIC) for *Escherichia coli*.

TABLE 2

| Sample No. | Powder No. | pH Regulator Solution (alkali solution) | Component (wt %) Ag | Component (wt %) Cl | Cl/Ag Molar Ratio | Light Resistance (WH) before sunlight irradiation | Light Resistance (WH) after sunlight irradiation | Heat Resistance (WH) before heating | Heat Resistance (WH) after heating | Antibacterial Property MIC (ppm) | Evaluation |
|---|---|---|---|---|---|---|---|---|---|---|---|
| 7 (Inv) | 7 | NaOH | 4.8 | 4.5 | 2.84 | 97 | 95 | 97 | 95 | 250 | good |
| 8 (Comp) | 8 | NaOH | 4.2 | 9.2 | 7.02 | 97 | 95 | 97 | 95 | 250 | good |
| 9 (Comp) | 9 | NaOH | 3.9 | 14.8 | 13.02 | 93 | 92 | 93 | 93 | 250 | bad |
| 10 (Comp) | 10 | NaOH | 3.5 | 1.08 | 0.92 | 93 | 82 | 93 | 93 | 500 | bad |
| 4 (Comp) | 4 | NaOH | — | — | — | 97 | 96 | 97 | 94 | ineffective | bad |
| 6 (Comp) | 5 | NaOH | 4.0 | — | — | 87 | 85 | 8Y | 87 | 250 | bad |

(Note)
Inv: Invention, Comp: Comparison

Table 2 shows the following. Samples 7 and 8 were excellent in antibacterial properties, light resistance, and heat resistance. Sample 9 had a slightly poor powder whiteness because of the high Cl/Ag ratio, although it was sufficiently effective in antibacterial properties. Sample 10 had slightly poor light resistance because of the low Cl/Ag ratio of 0.92. The above results are given together with the data for samples 4 and 6 for the purpose of comparison.

Table 3 provides a comparison among sample 11 (powder 11), samples 12 to 17 (powders 12 to 17), and samples 18 to 20 (powders 18 to 20) with respect to the effects of various chlorine compounds added as chlorine sources for the preparation of these powders on discoloration (judged visually), together with the effects of zinc nitrate and zinc oxide both used as sources of zinc as metal ions.

TABLE 3

| Sample No. | Powder No. | Compound added | pH Regulator Solution (alkali solution) | Component (wt %) Ag | Component (wt %) Cl | Cl/Ag Molar Ratio | Discoloration (24-hr sunlight irradiation) before irradiation | Discoloration (24-hr sunlight irradiation) after irradiation | Evaluation |
|---|---|---|---|---|---|---|---|---|---|
| 11 (Inv) | 11 | zinc chloride | NaOH | 3.2 | 6.7 | 6.60 | white | white | good |
| 12 (Comp) | 12 | zinc nitrate | NaOH | 3.6 | | | gray | black | bad |
| 13 (Comp) | 13 | zinc nitrate | NaOH | 3.8 | | | gray | black | bad |
| 14 (Comp) | 14 | zinc nitrate | NaOH | 4.3 | | | gray | black | bad |
| 15 (Comp) | 15 | zinc nitrate | NaOH | 3.5 | | | gray | black | bad |
| 16 (Comp) | 16 | zinc nitrate | NaOH | 3.3 | | | gray | black | bad |
| 17 (Comp) | 17 | zinc oxide | NaOH | 3.0 | | gray | black | bad | |
| 18 (Inv) | 18 | calcium chloride | NaOH | 2.9 | 5.2 | 5.58 | white | white | good |
| 19 (Inv) | 19 | magnesium chloride | NaOH | 3.0 | 5.6 | 5.84 | white | white | good |
| 20 (Inv) | 20 | aluminum chloride | NaOH | 2.8 | 5.1 | 5.68 | white | white | good |
| 21 (Inv) | 21 | hydrochioric acid | NaOH | 3.1 | 5.6 | 5.68 | white | white | good |

(Note)
Inv: Invention, Comp: Comparison

Table 3 shows the following. Sample 11 had excellent light and heat resistance because of the use of zinc chloride as a chlorine source. Samples 18, 19, and 20, for which calcium chloride, magnesium chloride, and aluminum chloride had been used as chlorine sources, also had excellent effects. In contrast, the samples produced using zinc compounds not providing chlorine ions, such as zinc nitrate and zinc oxide, were already gray prior to sunlight irradiation and turned black upon the irradiation, showing that they had poor light resistance.

While the invention has been described in detail and with reference to specific embodiments thereof, it will be apparent to one skilled in the art that various changes and modifications can be made therein without departing from the spirit and scope thereof.

What is claimed is:

1. A process for producing an antibacterial titania which comprises the steps of:
    (a) incorporating a salt of an antibacterial metal into a slurry of metatitanic acid to adhere ions of the antibacterial metal to titania in the metatitanic acid slurry, wherein the antibacterial metal is silver;
    (b) adding a source of chlorine ions to the resulting slurry of step (a), wherein the source of chlorine ions is selected from the group consisting of zinc chloride, calcium chloride, magnesium chloride, aluminum chloride and hydrochloric acid;
    (c) filtering the resulting slurry; and
    (d) drying the resulting residue of step (c) to obtain said antibacterial titania,
   wherein said salt of an antibacterial metal, said metatitanic acid, and said source of chlorine ions is sufficient to result in a final Cl/Ag molar ratio in a range of from 2.8 to 7.2 in said antibacterial titania.

2. The process of claim 1, wherein, after step (b) and prior to step (c), said process further comprises the steps of:

(b') adding a caustic alkali solution to the resulting slurry of step (b); and (b") maintaining the final pH of the resulting slurry of step (b') in a weakly alkaline range of from 7 to 9.

3. The process of claim 1, wherein the source of chlorine ions is zinc chloride.

4. Antibacterial titania produced according to the process of claim 3.

5. Antibacterial titania produced according to the process of claim 1.

* * * * *